United States Patent [19]

Barber et al.

[11] Patent Number: 4,950,480
[45] Date of Patent: Aug. 21, 1990

[54] ENHANCEMENT OF ANTIGEN IMMUNOGENICITY

[75] Inventors: Brian H. Barber, Mississauga; George Carayannotis, Scarborough, both of Canada

[73] Assignee: Connaught Laboratories Limited, Willowdale, Canada

[21] Appl. No.: 46,095

[22] Filed: May 5, 1987

[30] Foreign Application Priority Data

May 6, 1986 [GB] United Kingdom ............... 8610983

[51] Int. Cl.$^5$ .................. A61K 39/00; C08H 1/00; G01N 53/00
[52] U.S. Cl. ...................... 424/85.8; 424/88; 424/89; 424/92; 530/387; 530/391; 530/402; 530/403; 530/404; 530/405; 530/406; 435/7; 435/69.3; 435/172.2; 435/240.2
[58] Field of Search .............. 530/391, 357, 402–406; 424/85–88, 89, 92; 435/7, 68, 172.2, 240.2

[56] References Cited

U.S. PATENT DOCUMENTS 4,400,376 8/1983 Sanderson ........................ 424/88
4,634,590 1/1987 Cohen et al. ..................... 424/88

OTHER PUBLICATIONS

Hopkins et al, "Monoclonal antibodies to sheep lymphocytes, I. Identification of MHC class II molecules on lymphoid tissue and changes in the level of class II expression on lymph-borne cells following antigens stimulation in vivo," Immunology, vol. 59, pp. 433–438, 1986.

Stites et al "Basic and Clinical Immunology" Large Medical Publications, 5th, edition, pp. 71–85, 1984.

Lampson et al, "Two populations of Ia-like molecules on a human B cell line" Journal of Immunology, vol. 125 No. 1, pp. 293–299, 1980.

*Primary Examiner*—Garnette Draper
*Assistant Examiner*—Abdel A. Mohamed
*Attorney, Agent, or Firm*—Sim & McBurney

[57] ABSTRACT

A new method is described for eliciting IgG antibody response to proteins or synthetic peptides without the requirement for the use of adjuvants, thereby making it easier and safer to confer protection against pathogenic organisms. The antigen is coupled to a monoclonal antibody, specific for membrane determinants expressed on certain types of mammalian recipient cells, called antigen presenting cells. The monoclonal antibody acts as a "vector" or "delivery vehicle" for targeting foreign antigens onto such recipient cells. This targeting facilitates subsequent antigen recognition by helper T-cells, which are pivotal in helping the induction of antigen-specific IgG responses.

21 Claims, 5 Drawing Sheets

ENHANCEMENT OF ANTIGEN IMMUNOGENICITY

FIELD OF INVENTION

The present invention relates to a novel procedure for immunization against disease, and/or the generation of antibody responses in vivo without the use of adjuvants and to novel vaccine materials and conjugates used in the procedure.

BACKGROUND OF THE INVENTION

In the conventional method of protection against disease by vaccination, the central principle involves the injection or ingestion of a material that will elicit antibodies against said material, such that, when challenged later with a pathogenic organism containing homologous material, the individual to whom the material has been administered is protected against the pathogenic disease. The materials injected or ingested that have this property of eliciting antibodies are called antigens.

It has been known for many years that the immunogenicity (that is, its ability to elicit antibodies) of an antigen can be improved by the addition of so-called adjuvants. In some cases, materials that apparently have little or no immunogenicity have been made to make high titres of antibody in in vivo systems by the addition of an adjuvant. Some of these adjuvants are, however, highly toxic and can cause undesirable side effects or lesions. Aluminum hydroxide or aluminum phosphate are routinely used as adjuvants for human vaccines, but have been known to cause lumps at the site of injection. Freund's complete adjuvant (FCA), a mixture of a light petroleum oil and killed *Mycobacterium tuberculosis*, can often produce excellent titres for materials which do not normally give antibodies in vivo under any other conditions. Unfortunately lesions will often develop at the site of injection when using this material, making the procedure unacceptable for human use.

There are a number of other materials which have been investigated for use as adjuvants. In published European Patent Application No. 0149581, the use of muramyl di-peptide is disclosed. In published United Kingdom Patent Application No. 2,053,231, the use of a synthetic adjuvant consisting of tetrapeptides or pentapeptides is disclosed. In earlier patents, the use of oil emulsions is disclosed as having an adjuvanting effect. Unfortunately, it appears that the better a material is at behaving as an adjuvant to antigen immunogenicity, the worse are the side effects. For example, it has been shown that muramyl dipeptide is an excellent adjuvant but appears to have a number of undesirable properties which prevent its use in human vaccines.

In general, all the adjuvants presently in use in mammals fall into two distinct types. The first type involves the so-called "depot" effect and the second type depends on general immunological stimulation of the system under study. The adjuvants which rely on the depot effect are believed to bring the immune cells to the antigen site, where the depot effect relies on the injected antigen being trapped or insolubilized in a medium, giving sustained circulating levels. The second type of adjuvant, involving general stimulation of the immune system, appears to rely on an inflammatory reaction resulting in a series of cells being stimulated, such that any antigen has an improved chance of eliciting antibodies.

Current theories of immunology suggest that, in order to provide a potent antibody response, an antigen must be seen by both B cells, which subsequently develop into the antibody producing cells, and also by helper T-cells, which provide growth and differentiation signals to the antigen specific B-cells. Helper T-cells recognize the antigen on the surface of antigen-presenting cells (APC) in association with Class II major histocompatibility complex (MHC) gene products.

SUMMARY OF INVENTION

The present invention involves a new method of immunization which does not involve the use of unacceptable adjuvants. The present invention, in one aspect, provides a novel immunization method and takes advantage of the fact that both B-cells and APC of the macrophage lineage express Class II MHC gene products. Instead of injecting antigen in the presence of adjuvant, the antigen is coupled to a monoclonal antibody specific for a surface structure of antigen-presenting cells, including Class II MHC determinants and is injected in this form. By coupling it to the antigen, the monoclonal antibody is converted into a "vector" or "delivery vehicle" for targeting the antigen onto the relevant cells in the immune system. In effect, the method brings the antigen to the antigen-presenting cells rather than the other way around, as is thought to be the case when antigen is injected in the presence of Freund's complete adjuvant.

The present invention also provides, in another aspect, a novel vaccine for utilization in the novel immunization method comprising a conjugate of an antigen and a monoclonal antibody specific for a gene product of the major histocompatibility complex or other surface structure in a suitable carrier medium. The present invention, in a further aspect, provides the novel conjugate.

The present invention uses a new method of enhancing the immunogenicity of weak antigens, which does not involve the use of unacceptable adjuvants, is therefore much safer and can be used for materials that are not normally very antigenic. An example of such materials are small peptides which are epitopes of larger proteins or are protein subunits of the pathogens themselves. Epitopes are parts of a larger antigen which represent the immunological recognition sites within the structure. The vaccination method of the invention, therefore, can avoid the injection of killed or attenuated organisms, that can have unfortunate side effects, by the use of such epitopes or protein subunits in the form of conjugates with targeting monoclonal antibodies.

DESCRIPTION OF INVENTION

In the present invention, an antigen, against which it is desired to raise antibodies in the body, is coupled to a monoclonal antibody, which is specific for a surface structure of antigen-presenting cells, including a gene product of the major histocompatibility complex (MHC). This allows for a concentration of the antigen to the relevant cells in the immune system upon injection of the coupled material. The derivatised antibody, therefore, acts as a "vector" or "delivery vehicle" for targeting antigenic determinants onto the macrophage cells, thereby facilitating their recognition by the T-helper cells. The presenting cells possess a variety of specific cell surface structures, including Class I and Class II histocompatibility gene product. Thus, antigens may be coupled to a monoclonal antibody specific for of the surface structures on the antigen presenting cells, including Class I and Class II MHC gene products.

One specific example of a coupling useful in the present invention is the antigenic protein avidin and the monoclonal antibody specific for the I-A$^k$ Class II major histocompatibility determinants. It is understood that this example is but one application of the general principle of the present invention discussed above.

In such specific example, monoclonal antibodies specific for the I-A$^k$ Class II major histocompatibility determinants may be prepared from a suitable hybridoma cell line. To permit easy conjugation with other proteins, the antibodies preferably are biotinylated, prior to exposure to the appropriate protein, in this example avidin. Avidin binds with high affinity to the biotinylated antibody, and has previously been characterized as an antigen. Varying doses of this conjugate were used to treat a strain of mice expressing the I-A$^k$ determinants. Mice of a different strain expressing only I-A$^b$ determinants were used as controls. The results of these experiments, given in detail in the Examples below, showed that avidin, when presented as an antigen in this manner and in very low quantities can be made highly immunogenic in the absence of a standard adjuvant. If equivalent quantities of free avidin were mixed with non-biotinylated antibody (so that no conjugation occurred), no antibody response was elicited, indicating that the result was conjugate dependant. Recognition of the I-A$^k$ determinants was essential, since avidin conjugated to an antibody of irrelevant specificity was not effective in eliciting an antibody response. In other experiments, also detailed in the Example below, a monoclonal antibody that is specific for the Class I MHC conjugated to avidin also showed an immunogenic response and generated antibodies to avidin.

The conjugates which are employed in the present invention are not limited to conjugates of a single antigen with the monoclonal antibody but include conjugates where two or more antigenic proteins or peptides are conjugated to the monoclonal antibody.

In specific examples, biotinylated monoclonal antibody may be conjungated to avidin and bovine serum albumin or to avidin and a Herpes synthetic peptide. These conjugates were formed and used to immunize mice. The Herpes peptide is part of the Herpes simplex virus glycoprotein D. In these experiments, reported in detail in the Examples below, it was found that antibodies were raised against bovine serum albumen and the Herpes peptide, as well as against the avidin. Replacement of the avidin by another protein, namely streptavidin, which also has high binding affinity to biotin, provided a good response, indicating that the targeting effect is not restricted to avidin and that there was no serological cross-reaction of anti-streptavidin antibodies with avidin.

It has also been shown in experiments reported in the Examples below that the response of mice to cumulative injections of a complex consisting of antibody-avidin-peptide is equivalent to the response using Freund's complete adjuvant. This latter experiment indicates that vaccines can be constructed using peptide antigens that elicit antibodies that can be neutralising and protective against the pathogen from which the peptide is extracted.

It is evident from the above that the invention may be used as a method of immunization in vivo and in vitro for making hybridomas, and thus specific monoclonal antibodies. Such specific antibodies have a wide range of use both in medicine and immunology.

In the following specific Examples, the efficacy of the invention is demonstrated for three immunologically-unrelated protein antigens namely avidin, streptavidin and bovine serum albumin. In addition, the use of the method resulted in generation of IgG antibodies against a synthetic peptide from the glycoprotein D of herpes-simplex virus. In addition, an immunogenic response has been achieved using MAbs against Class I and Class II determinants of MHC. This data demonstrates the generality of the invention in application to the use of any conjugate of an antigen and a monoclonal antibody specific for surface structures on APC.

EXAMPLES

EXAMPLE I

This Example illustrates the preparation of biotinylated monoclonal antibodies and conjugates thereof with avidin.

Hybridoma cell lines TIB-92 (anti-I-A$^k$) and HB-65 (anti-influenza A NP, the control antibody) were obtained from the American Type Culture Collection (ATCC), Rockville, Md., U.S.A. and were cultured in RPMI 1640 culture medium, supplemented with 10% fetal calf serum, L-glutamine and antibiotics. The antibodies produced by these cell lines are both of the IgG2a subclass, and were purified from culture supernatants by conventional protein A-Sepharose chromatography.

The purified antibodies then were biotinylated using the general method described by Goding in "Monoclonal Antibodies: Principles and Practice" (1983) Academic Press, London. For this method, the antibodies were dialysed against 0.1M sodium bicarbonate solution at pH 8.2, and concentrated to 1.0 mg/ml immediately before use. Biotin succinimide ester (Sigma Chemical Co.) was dissolved in dimethyl sulphoxide to a concentration of 1 /ml, immediately before use. 60 μl of this ester solution were added per ml of antibody solution at room temperature and left for 1 hour. The biotinylated protein was dialysed overnight against phosphate buffered saline (PBS) and stored at 4° C.

The biotinylated antibody prepared as just described was mixed with avidin in a ratio of 2 moles of antibody to 1 mole of avidin to form a biotinylated antibody-avidin conjugate for each of the antibodies.

EXAMPLE II

This Example illustrates the immunogenic response of the conjugates prepared as described in Example I in mice.

Two different strains of mice (namely (B6×C3H)F$_1$ and B6 in groups of three were injected with the conjugates prepared as described in Example I as well as a mixture of antibody and avidin and of avidin alone according to the schedule contained in the following Table I:

TABLE I

| | | Immunization Protocol | |
|---|---|---|---|
| Group | Priming Antigen | Priming avidin dose (ug) | Adjuvant (FCA) |
| I | (bio-anti-I-A$^k$)—Avidin* | 5 | — |
|  | (bio-anti-I-A$^k$)—Avidin* | 50 | — |
| II | anti-I-A$^k$ + Avidin | 5 | — |
|  | " | 50 | — |
| III | (bio-anti-NP)—Avidin+ | 5 | — |
|  | (bio-anti-NP)—Avidin+ | 50 | — |
| IV | Avidin | 5 | +/— |
|  | " | 50 | +/— |

Notes:
* = Biotinylated
+ = In Group III, antigen was injected only into (B6 × C3H)F$_1$ mice
NP = nucleoprotein
FCA = Freund's complete adjuvant The injections consisted of subcutaneous inoculations of 0.2 ml of the various solutions and after 21 days mice in all the groups were boosted with an intraperitoneal injection of 5 μg of avidin in 0.2 ml of PBS. Nine days later the mice were bled from the retro-bulbar sinus and their sera stored at 4° C.

The immune sera were tested for anti-avidin activity as follows: Avidin solution (50 μl) at a concentration of 20 μg/ml was added to the wells of a polyvinyl microtitre plate and incubated for 1 hour, after which the plates were washed. The plates then were incubated with a 1% solution of bovine serum albumin (BSA) in PBS for an additional 1 hour. The BSA-buffer was removed and 50 μl of serial dilutions of the immune sera in 1% BSA-PBS were added to each well and incubated for 1 hour. The plates were then washed three times with 1% BSA-PBS and then each well treated with 50 μl of $^{125}$I-protein A for 1 hour. The plates then were washed twice with buffer and the individual wells counted in a gamma counter.

Figure 1:
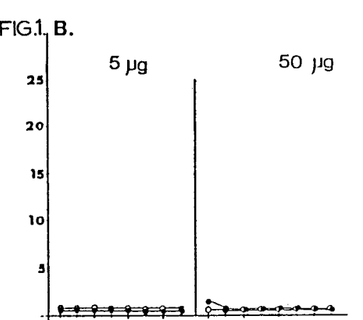
FIG. 1 contains graphical representations, labelled A to D, of the anti-avidin responses in mice in one series of experiments described in the Examples below.

The anti-avidin response of immune sera were plotted graphically and appear as FIG. 1. In this FIG. 1, the anti-avidin responses of the immune sera from groups I, II, III and IV (Table I) respectively are shown in A, B, C and D. The open circle line is the response in (B6×C3H)F$_1$ mice while the closed circle line is the response in B6 mice.

As may be seen from the data presented in FIG. 1, at the 5 μg dose of avidin, a significant response was observed in (B6xC3H)F$_1$ mice injected with (anti-I-A$^k$)-avidin conjugate (FIG. 1A, open circles) whereas the B6 mice (FIG. 1A, closed circles), which do not have the particular surface antigens for which the antibody was made, were not appreciably sensitized (see FIG. 1A). This result cannot be attributed to an immunostimulating effect of the antibody alone, since the mixture of 5 μg of avidin with unmodified anti-I-A$^k$ MAb did not elicit a response (FIG. 1B). An equal amount of avidin coupled to the control anti-NP MAb also failed to generate an appreciable response (FIG. 1C), indicating that the positive response shown in FIG. 1A is due to more than a simple conjugation of avidin to an antibody. As expected 5 μg of avidin injected with Freund's complete adjuvant induced a strong serological response (FIG. 1D). At the 50 μg of avidin dose, free avidin in the absence of adjuvant failed to stimulate a response (FIG. 1B), but in the form of (bio-anti-I-A$^k$)-avidin, the conjugate sensitized both (B6×C3H)F$_1$ and B6 mice (FIG. 1A). Responses in the B6 mice are likely a reflection of the elevated reactivity of the avidin-MAb conjugate on the B6 targets and may be attributed either to cross-reactivity of the conjugated MAb or more efficient APC uptake of the MAb-avidin complex.

These results demonstrate that a low dose of avidin (i.e., 5 μg) can be made immunogenic in the absence of adjuvant when presented to the immune system coupled to a monoclonal antibody specific for recipient class II major hisocompatibility determinants, namely the anti-I-A$^k$ MAb.

Figure 2:
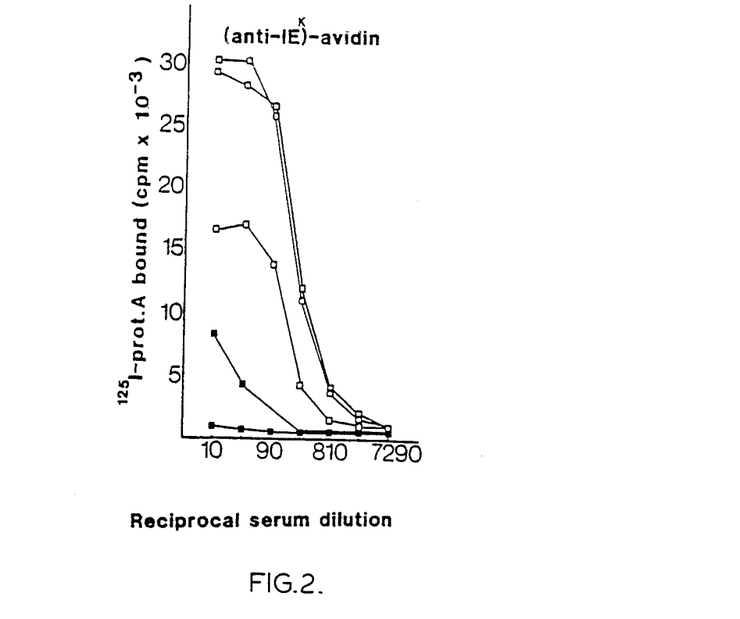
FIG. 2 is a graphical representation of secondary anti-avidin responses in mice in another series of experiments described in the Examples below.

The test procedure was repeated using a different anti-Class II MAb, in this case an anti-I-E$^k$ as the targeting MAb. The results obtained were plotted graphically and are reproduced in FIG. 2. As may be seen therein, individual (B6×C3H)F$_1$ mice (open squares) immunized with the (anti-I-E$^k$)-avidin conjugate gave a 7 to 9 fold higher response than the B6 mice (closed squares) that received the same dosage of conjugate. Unconjugated mixtures of avidin and the MAb gave only background levels of reactivity and this data is not presented.

EXAMPLE III

This Example illustrates the use of antibody-biotin-avidin conjugates to raise antibodies to a third party protein.

A conjugate of anti-I-A$^k$ antibody, avidin and bovine serum albumin (BSA) was formed by mixing equimolar amounts of biotinylated monoclonal antibody (prepared as described in Example 1), avidin and biotinylated bovine serum for 20 minutes at 20° C. The mixture then was centrifuged for five minutes at 12,000 g to remove any precipatable aggregates. Mice were injected subcutaneously with this complex (approx. 30 μg BSA) in a similar regime to those in Example II, and, after three weeks, were boosted with an intraperitoneal injection of 10 μg of free BSA in PBS. Sera from the mice were obtained nine days later and assayed in a manner similar to the samples in Example II. The blocking buffer in the radioimmune assay contained 0.1% ovalbumin in PBS and 65,000 cpm of $^{125}$I-Protein A were added to each assay well.

Figure 3:
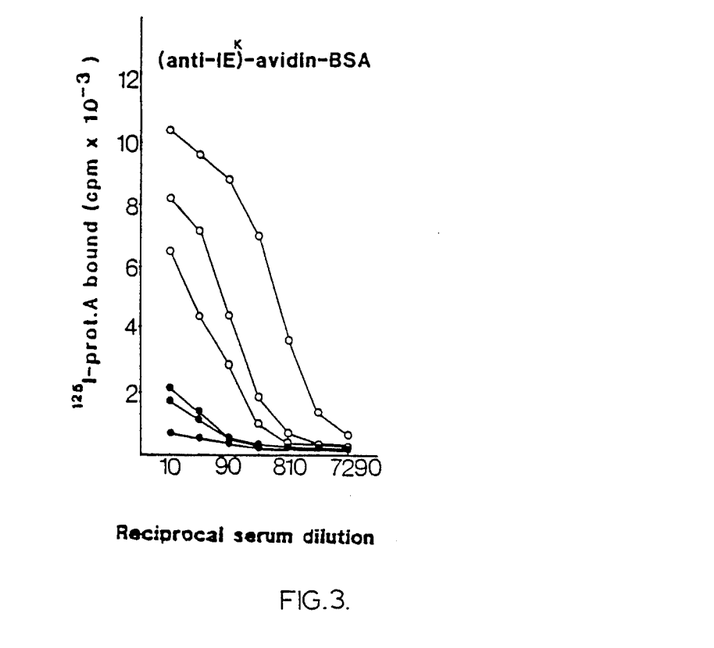
FIG. 3 contains graphical representations of anti-bovine serum albumin responses in mice in a further series of experiments described in the Examples below.

The results obtained were plotted graphically and appear as FIG. 3. The open circle lines define the response in individual (B6×C3H)F$_1$ mice while the closed circle lines represent the response in B6 mice. No response was observed in mice injected with an equivalent dose of avidin in an unconjugated mixture of non-biotinylated Mab and avidin and this data is not presented. As may be seen in FIG. 3, a considerable response to bovine serum albumin was observed. These data indicate the practicality of obtaining a serological response to any third party protein simply by coupling it to the MAb-avidin complex. This would allow for the preparation of any number of adjuvant free subunit protein, vaccines, that would avoid problems connected with the parent organism of the subunit protein.

EXAMPLE IV

This Example illustrates the use of antibody-biotin-avidin conjugates to raise antibodies to a small peptide.

Figure 4:
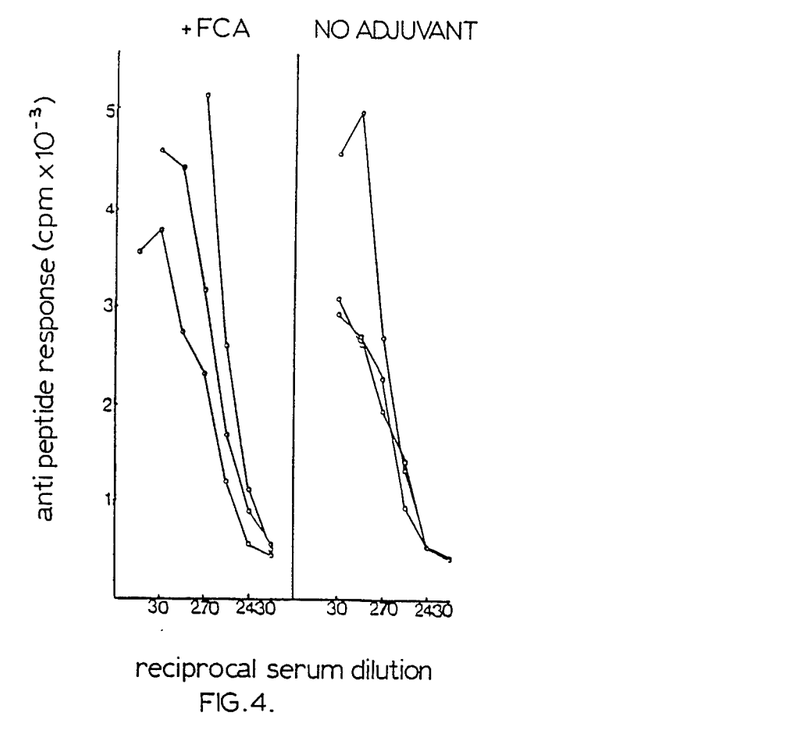
FIG. 4 contains graphical representations of secondary antibody responses to a synthetic Herpes peptide in mice in another series of experiments described in the Examples below.

A biotin mediated conjugate was made between anti-I-$A^k$ and avidin to which the Herpes synthetic peptide was coupled. The Herpes peptide used was an N-terminal peptide (12-20) from glycoprotein D of Herpes simplex virus and was photocoupled to avidin using the benzoyl-benzoyl-glycine linker moiety with a molar ratio of the peptide to avidin of 8.1. The peptide was synthesized and consisted of nine amino acids. After a course of three weekly injections of 30 μg of the anti-I-$A^k$-avidin-peptide conjugate into (B6×3H)$F_1$ mice, the mice were boosted once with avidin-(herpes peptide) intraperitoneally and then sera were collected nine days after the booster injection. The results are shown in FIG. 4. The illustrated results represent the net antibody response to Herpes peptide after subtracting the binding on the control samples and compared to the response obtained with a single priming in Freund's complete adjuvant (FCA) followed by the same booster injection.

EXAMPLE V

This Example illustrates the use of antibody-biotin-streptavidin complexes raise antibodies to streptavidin.

Figure 5:
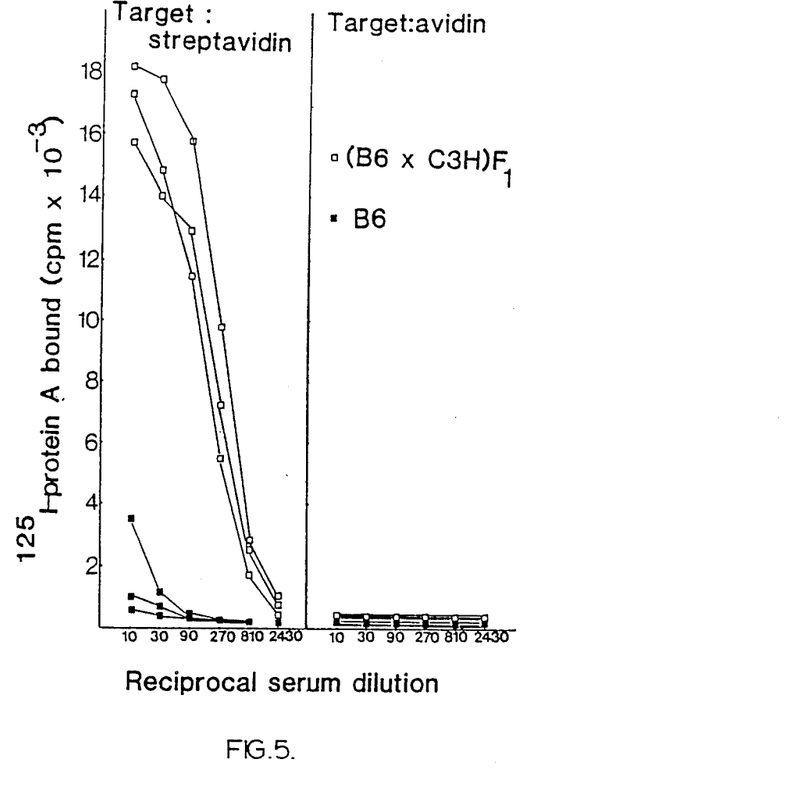
FIG. 5 contains graphical representations of secondary antibody responses to streptavidin and avidin in mice in a yet further series of experiments described in the Examples below.

Streptavidin is a protein which was extracted from *Streptomyces avidinii*. This protein material was conjugated with the anti-I-$A^k$ biotinylated" antibody following the procedure generally described above in Example I and the conjugate was injected into (B6×C3H)$F_1$ and B6 mice, in the manner described in Example II. Sera from these mice responded to streptavidin but were negative when assayed against avidin. These results appear graphically for individual mice in FIG. 5.

These results show that the targeting effect is not restricted to avidin, but is obtained with another serologically non-cross biotin-binding active protein.

EXAMPLE VI

This Example illustrates the enhancement of avidin immunogenicity using monoclonal antibodies specific for Class I MHC's.

Figure 6:
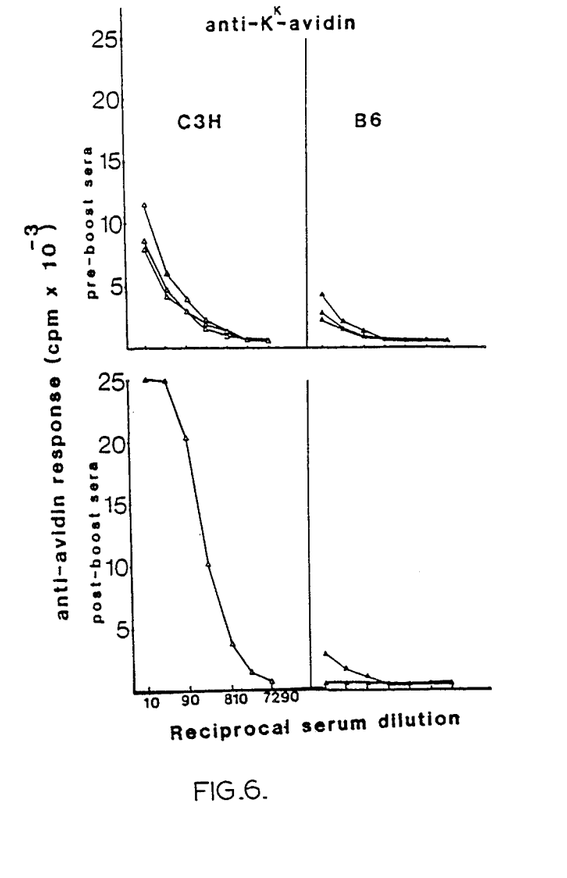
FIG. 6 contains graphical representations of antibody responses to avidin in mice in one more series of experiments described in the Examples below.

Using a method similar to Example I, avidin was coupled to biotinylated anti-$K^k$ monoclonal antibody. This material (30 μg) was used to prime female- C3H (H-$2^k$) or B6 (H-$2^b$) mice. Three weeks later the mice were bled to obtain preboost sera and then subsequently were boosted with avidin. The results appear in FIG. 6. As may be seen therein the C3H mice (open triangles) gave a higher anti-avidin response than B6 mice (closed triangles), indicating that there was specific delivery of avidin only in mice expressing the $K^k$ determinants. These results illustrate that it is possible that any monoclonal antibodies directed against APC determinants can mediate antigen delivery even when these determinants are not restricted only to APC.

SUMMARY OF DISCLOSURE

In summary of this disclosure, the present invention provides a novel method of vaccinating mammals by the conjugation of antigens, which may be in the form of synthetic epitopes or protein subunits, to monoclonal antibodies specific for major histocompatibility complex antigens of the recipient, such that these antigen-antibody complexes may be used to elicit a beneficial antibody response without needing to use deleterious adjuvants. Modifications are possible within the scope of this invention.

What is claimed is:

1. A novel conjugate physiologically suitable for administration to a mammal to elicit an immune response, comprising at least one antigen which is a peptide or protein bonded to a monoclonal antibody specific for a histocompatibility antigen present on the surface of B-cells and macrophages.

2. The conjugate of claim 1, wherein said monoclonal antibody is specific for a gene product of the major histocompatibility complex.

3. The conjugate of claim 2, wherein said monoclonal antibody is specific for Class II molecules of the major histocompatibility complex determinants.

4. The conjugate of claim 2, wherein said monoclonal antibody is specific for Class I molecules of the major histocompatibility complex determinants.

5. The conjugate of claim 1, wherein different antigen molecules are bonded to said monoclonal antibody, to elicit an immune response to each of said antigen molecules upon administration.

6. The conjugate of claim 1 wherein said antigen comprises a weakly-immunogenic molecule.

7. The conjugate of claim 6 wherein said weakly-immunogenic molecule is a synthetic peptide comprising an amino acid sequence to the epitope of an antigen molecule of the pathogenic organism.

8. The conjugate of claim 6 wherein said weakly-immunogenic molecule comprises an epitope of the protein sub-unit.

9. A vaccine physiologically suitable for administration to a mammal to elicit an IgC antibody response to an antigen, which consists essentially of a conjugate comprising a normally weakly-immunogenic antigen which is a peptide or protein bonded to a monoclonal antibody specific for a histocompatibility antigen present on the surface of B-cells and macrophages and a suitable carrier therefor, whereby said antibody response occurs without an immunogenicity-enhancing adjuvant.

10. The vaccine of claim 9, wherein said monoclonal antibody is specific for a gene product of the major histocompatibility complex.

11. The vaccine of claim 10 wherein said weakly-immunogenic antigen comprises a weakly-immunogenic peptide or protein.

12. The vaccine of claim 11 wherein said weakly-immunogenic peptide is a synthetic peptide comprising an amino acid sequence to the epitope of an antigen molecule of the pathogenic organism.

13. The vaccine of claim 11 wherein said weakly-immunogenic protein is an epitope of protein sub-unit.

14. A method of immunization of a mammal against a pathogenic disease by the administration to the mammal at least one antigen which elicits an antibody response to said pathogenic disease, which comprises administering said antigen in the form of a conjugate wherein said 
antigen is a peptide or protein and is bonded to a monoclonal antibody specific for a histocompatibility antigen present on the surface of B-cells and macrophages.

15. The method of claim 14 wherein said monoclonal antibody is specific for a gene product of the major histocompatibility complex to elicit IgG antibody response to the antigen.

16. The method of claim 15 wherein said monoclonal antibody is specific for Class II molecules of the major histocompatibility complex determinants.

17. The method of claim 15 wherein said monoclonal antibody is specific for Class I molecules of the major histocompatibility complex determinants.

18. The method of claim 14 wherein said conjugate comprises different tandemly linked antigen molecules to elicit an immune response to each of said antigenic molecules.

19. The method of claim 15 wherein said antigen is a weakly immunogenic peptide or protein whose immunogenicity is significantly enhanced by said bonding to said monoclonal antibody, whereby said IgG antibody response to said antigen, occurs without immunogenicity-enhancing adjuvants.

20. The method of claim 19 wherein said weakly-immunogenic peptide or protein is a synthetic peptide comprising an amino acid sequence to the epitope of an antigen molecule of the pathogenic organism.

21. The method of claim 19 wherein said weakly-immunogenic peptide or protein is a sub-unit protein comprising an epitope of an antigen protein molecule of the pathogenic organism.

* * * * *